United States Patent [19]

Tosk

[11] 4,287,027

[45] Sep. 1, 1981

[54] METHOD OF DETERMINING THE CONCENTRATION OF REDUCING AGENTS

[76] Inventor: Jeffrey M. Tosk, 3235 Cambridge Ave., Bronx, N.Y. 10463

[21] Appl. No.: 151,687

[22] Filed: May 20, 1980

[51] Int. Cl.³ .................... G01N 27/30; G01N 27/52
[52] U.S. Cl. ................................ 204/1 T; 204/195 R; 204/291
[58] Field of Search .............. 204/1 N, 290 F, 1 T, 204/195 R, 1 Y, 1 B, 291, 292; 429/40, 41, 44, 45

[56] References Cited

U.S. PATENT DOCUMENTS

| | | | |
|---|---|---|---|
| 3,592,694 | 7/1971 | Urbach et al. ............... 204/1 T UX |
| 3,663,414 | 5/1972 | Martinsons et al. ............. 204/290 F |
| 3,761,385 | 9/1973 | Ruthel et al. .................... 204/290 F |
| 3,773,555 | 11/1973 | Cotton et al. ............... 204/290 F X |
| 3,992,267 | 11/1976 | Oswin et al. ...................... 204/1 T |
| 4,201,634 | 5/1980 | Stetter .................................. 204/1 T |
| 4,207,162 | 6/1980 | Lotze ............................... 204/195 R |

*Primary Examiner*—G. L. Kaplan
*Attorney, Agent, or Firm*—Amster, Rothstein & Engelberg

[57] ABSTRACT

The quantitative analysis of strong reducing agents is determined by measuring the electrode potential created by an oxidation-reduction reaction occurring at an electrode assembly having an active electrode formed from a mixture of finely divided platinum and platinum oxide. The electrode assembly has been found to be particularly sensitive in determining the concentration of hydrazine and hydrazine containing compounds.

8 Claims, 4 Drawing Figures

METHOD OF DETERMINING THE CONCENTRATION OF REDUCING AGENTS

DESCRIPTION OF THE INVENTION

This invention relates in general to an electrode assembly and more particularly, to an electrode assembly for determining the concentration of strong reducing agents including hydrazine and hydrazine containing compounds by measuring the electrode potential created by an oxidation-reduction reaction.

Strong reducing agents are generally toxic chemicals which have important industrial application. In spite of their toxicity, these reducing agents are in widespread use throughout the chemical industry. The widespread use of these chemicals has imposed a serious health hazard upon the workers who are exposed to these chemicals on a daily basis. To provide for the safety of the workers, various Federal Agencies have established maximum concentration levels of these chemicals that the workers may be exposed to in the working environment. One effective way to control the chemical concentration in the work environment is to provide a continuous toxic chemical concentration monitoring system. Of the various reducing agents that are used in industry, hydrazine is known to be one of the more important ones due to the number of application in which it is used.

Hydrazine as a known toxic chemical is also known to be a cancer causing agent. In spite of its extreme toxicity, hydrazine is an important industrial chemical which has found general application in the pesticide and agricultural industry, as a reducing agent for use in rocket fuels, and as an intermediate chemical for the synthesis of pharmaceuticals and other organic chemicals. Humans exposed to low levels of hydrazine have been known to develop adverse body symptoms and prolonged or excessive exposure could ultimately result in death.

Present known methods for monitoring the toxic concentration of these reducing agents, such as hydrazine, are generally limited to gas and liquid chromatography following dirivitization. For example, these methods usually require relatively expensive and cumbersome chromatography equipment which makes the monitoring of the hydrazine concentration within a selected working environment in real-time impractical. Consequently, repetitive environment samples must be taken at the various locations within the work area, and continuously over the work period to determine the daily chemical exposure. Further, known monitoring methods and equipment are of a limited accuracy having a detection limit of usually one nanogram. Thus, workers can be exposed to cumulative dosages of hydrazine which are generally undetectable by the prior art methods and equipment.

There is therefore a need for a real-time detector that can be used to monitor the environment for even the lowest levels of toxic reducing agents such as hydrazine to provide a safe working environment.

It is broadly an object of this invention to provide an electrode assembly and method for determining the concentration of strong reducing agents such as hydrazine which overcomes or avoids one or more of the disadvantages of conventional chemical monitoring equipment. Specifically, it is within the contemplation of this invention to provide an electrode assembly for monitoring the concentration of strong reducing agents such as hydrazine and hydrazine containing compounds when present in an electrolyte solution.

A further object of this invention is to provide an electrochemical detector that is inexpensive and portable, to be used at multiple work stations for monitoring the concentration of toxic reducing agents present throughout the work environment.

A still further object of this invention is to provide a hydrazine detector that can continuously monitor the concentration of hydrazine in real-time at multiple work stations.

A still further object of this invention is to provide an electrochemical detector that does not require an independent source of power for its operation in determining the concentration of a strong reducing agent, including hydrazine and its derivatives.

In accordance with one embodiment of this invention, there is provided an electrode assembly for determining the concentration of reducing agents including hydrazine and compounds containing hydrazine by measuring the electrode potential created from an oxidation-reduction reaction occurring at the electrode assembly. The electrode assembly includes an active electrode formed from a mixture of finely divided platinum and platinum oxide constructed and arranged to retain its structural integrity during use, and a counter-electrode spaced proximate to the active electrode.

In accordance with the above embodiment there is further provided an electrochemical detector for determining the concentration of reducing agents such as hydrazine and compounds containing hydrazine by measuring the electrode potential created from an oxidation-reduction reaction occurring within the detector. The detector includes a housing having an inlet and outlet for passing a sample fluid between an electrode assembly. The electrode assembly includes an active electrode formed from a compressed mixture of finely divided platinum and platinum oxide constructed and arranged to retain its structural integrity during use. A counter-electrode is located within the housing proximate to the active electrode. The electrodes are electrically connected to a device for measuring the electrode potential created and determining the concentration of the reducing agent present.

The above brief description as well as further objects and features and advantages of the present invention will be more fully understood by reference to the following detailed description of a presently preferred but nonetheless illustrative, electrode assembly and method of determining the concentration of reducing agents including hydrazine in accordance with the present invention when taken in conjunction with the accompanying drawings, wherein.

Figure 1:
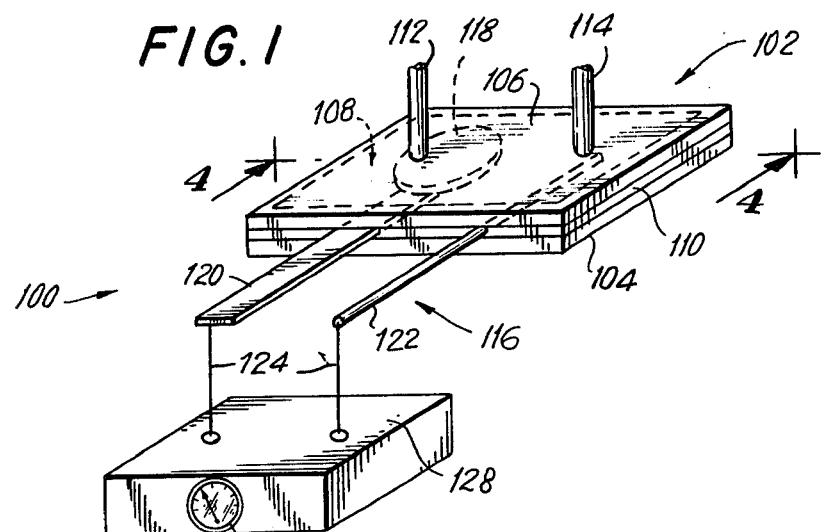
FIG. 1 is a perspective view of an electrochemical detector including a housing having a sample fluid inlet and outlet for determining the concentration of a reducing agent such as hydrazine, an electrode assembly within the housing electrically connected to an amplifier and indicating meter for visually monitoring the concentration of the reducing agent present.
Figure 2:
FIG. 2 is a perspective view of an electrode assembly which includes an active electrode in the form of a disk, formed from a compressed mixture of finely divided platinum and platinum oxide, and a counter-electrode spaced proximate to the active electrode.
Figure 3:
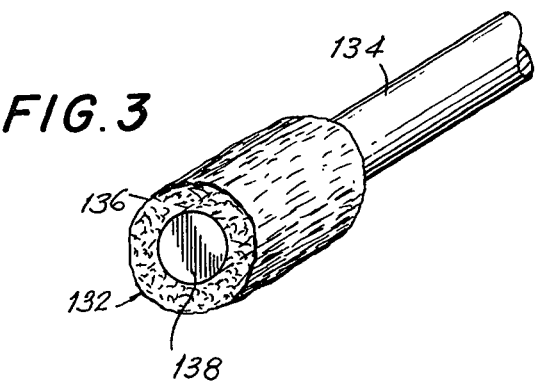
Figure 4:
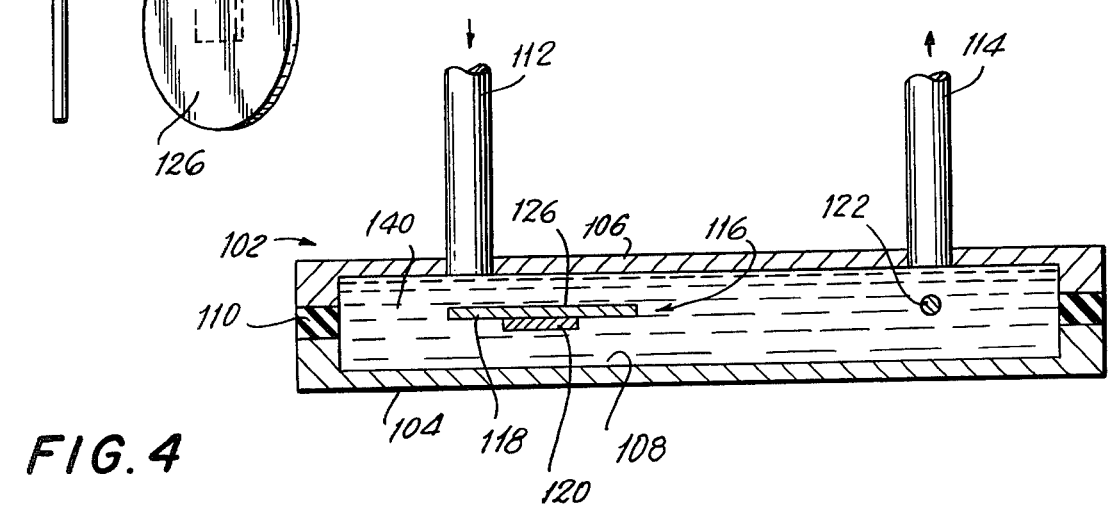

FIG. 3 is a perspective view of another embodiment of the active electrode of FIG. 2 including a layer of a mixture of finely divided platinum and platinum oxide held together by an electrically conductive resin on the end of an electrically conductive wire having an annular end region exposed to form a point probe; and FIG. 4 is a side sectional view taken along line 4—4 of FIG. 1 showing the active electrode and counter-electrode in operative relationship with an electrolyte solution containing a sample quantity of a reducing agent.

Referring specifically to FIG. 1, there is illustrated an electrochemical detector generally designated by reference to numeral 100 for determining the concentration of strong reducing agents including hydrazine and hydrazine containing compounds which are particularly known to be toxic. The detector 100 is generally constructed of a housing 102 which although illustrated as rectangular in shape, other geometric configurations for the housing may be provided, such as square, round, oval and triangular. The housing 102 is constructed of a lower half 104 and an opposite generally coextensive upper half 106. The lower and upper halves 104, 106 are further constructed and arranged such that when they are assembled in coextensive relationship with their recess in opposed relationship, a central cavity 108 is formed therebetween as bound by the surfaces of the lower and upper halves.

The housing 102 is sealed to provide a leak-free cavity 108 by sealing the lower and upper halves 104, 106 together by a suitable gasket or adhesive material 110 provided along the mating edges of the lower and upper halves when assembled in coextensive relationship. Access to the cavity 108 is provided by an inlet 112 and an outlet 114. The inlet and outlet 112, 114 are provided as tubes extending through the upper half 106 of the housing 102 to communicate with the cavity 108. The inlet and outlet 112, 114 are spaced from each other such that a sample fluid containing the reducing agent upon entering through the inlet, will flow substantially through the cavity 108 before reaching the outlet. Alternatively, the inlet and outlet 112, 114 may be placed within the lower half 102 or one each in the respective upper half 106 and lower half 104.

The housing 102 is constructed of material that is inert to the corrosive action of the reducing agent, such as glass. Located within the cavity 108 and disposed between the inlet and outlet 112, 114 is an electrode assembly 116 which is best shown in FIG. 2. In general, the electrode assembly 116 includes an active electrode 118 attached to a contact lead 120 and a counter-electrode 122. The active electrode 118 is placed within the cavity 108 adjacent to the inlet 112. The counter-electrode 122 is placed within the cavity 108 adjacent the outlet 114 and spaced an operative distance from the active electrode 118. The contact lead 120 and a portion of the counter-electrode 122 extend through the side of the housing 102 between the lower and upper halves 104, 106. The sample fluid containing the reducing agent within the cavity 108 of the detector 100 is prevented from leaking out around the contact lead 120 and counter-electrode 122 by the gasket or adhesive material 110 used to seal the lower and upper halves 104, 106 together as previously described.

The contact lead 120 and counter-electrode 122 are electrically connected to an amplifier 128 by wires 124, 124. The electrode potential created within the detector 100 is transmitted to the amplifier 128 for amplification to a voltage of sufficient level for recording on the indicating meter 130. However, it is to be noted that when a sufficiently high concentration of a strong reducing agent such as a hydrazine is present, the detector 100 will produce a sufficient flow of electrons between the electrode assembly that the concentration can be determined accurately using a standard current or volt meter without the need for amplification. Alternatively, the amplified signals from the amplifier 128 may be transmitted to a computer, alarm bell, flashing light, strip-recorder or other devices for signaling, recording and determining the concentration of the reducing agent within the sample fluid within the detector 100.

Referring to FIG. 2 the electrode assembly 116 is illustrated as including an active electrode 118 attached to a contact lead 120 and a counter-electrode 122. The counter-electrode 122 is constructed of an electrically conductive wire that is chemically inert to the reducing agent to be detected, such as platinum, gold, palladium, rhodium and ruthenium. In the preferred embodiment, the counter-electrode 122 is constructed of a platinum wire about 0.127 mm in diameter.

The active electrode 118 is fabricated from a compressed mixture of finely divided platinum and platinum oxide. A homogeneous mixture of platinum oxide in the form of a finely divided powder and platinum in the form of a finely divided sponge is prepared such as by ultrasonic mixing. The use of platinum sponge is preferred to platinum powder as it has a high surface area in relationship to its volume. However, finely divided platinum powder can also be used according to this invention. The homogeneous mixture is placed within the cavity of a die and compressed into the shape of a disk, generally between 2 mm and 20 mm in diameter, being limited only by the size of the cavity 108 of detector 100. The disk of the active electrode 118 has a large surface area 126 upon which the oxidation-reduction reaction occurs. The mixture is compressed from between 2,000–20,000 pounds per square inch, depending upon the ratio of platinum sponge to platinum oxide. The higher the weight percentage of platinum oxide in the mixture, the higher the compressive force needed to compress the mixture to provide an active electrode 118 which will maintain its structural integrity during use.

The selection of the weight percentage ratio of platinum sponge to platinum oxide in the mixture requires taking into consideration several factors. One factor is the mechanical strength of the active electrode 118 such that it will maintain its structural integrity during use. It has been found that the active electrode 118 can be fabricated from a mixture of platinum sponge and platinum oxide in the weight ratio of from 1/1–20/1. When the ratio of platinum sponge to platinum oxide is in the range of from 1/1–4/1, it has been found that the mechanical strength of the compressed active electrode 118 is generally insufficient to maintain its structural integrity during use. To increase the mechanical strength of the active electrode 118, a conductive water resistent thermoplastic or thermosetting resin that is inert to the reducing agent is included in the mixture of platinum sponge and platinum oxide to an amount up to about 20% by weight. Such conductive resins are well known and may include platinum powder mixed with a suitable epoxy resin. The use of a conductive resin will therefore not adversely decrease the electrical conductivity of the active electrode 118 when used in a manner only sufficient to bind the platinum sponge and platinum oxide together. The use of a thermoplastic or thermosetting resin, also allows the active electrode 118 to be fabricated by molding in a suitable shaped mold in the final configuration of the active electrode instead of the need for using a die and high compressive forces.

A second factor to take into consideration is that the sensivity of the detector 100 is somewhat dependent upon the oxidation-reduction reaction occurring with the platinum oxide on the surface area 126 of the active electrode 118. As the ratio to platinum sponge to platinum oxide increases, the surface concentration of platinum oxide decreases such that where the platinum sponge to platinum oxide ratio is greater than 20/1, the decreased sensivity of the active electrode 118 renders its generally impractical for detecting the presence of low levels of the reducing agent such as hydrazine as desired. In the preferred embodiment according to this invention, the weight ratio of platinum sponge to platinum oxide is found to be about 7/1. At this selected ratio, the active electrode exhibits good electrical properties in addition to having excellent mechanical strength such that it maintains its structural integrity during use over extended periods.

The active electrode 118 has been described as being fabricated from a mixture of platinum sponge and platinum oxide. As thus described, finely divided platinum sponge is selected and preferred over finely divided platinum powder due to the high porosity of the platinum particles when in the form of a sponge. The effect of the high porosity of the platinum sponge is to give the surface of the active electrode 118 a substantial increase in surface area 26 which results in a greater sensitivity of the detector 100 to low levels of the reducing agent to be detected. Platinum powder can also be used in the mixture as noted except that the active electrode 118 as thus constructed will have about ⅓ less sensitivity over active electrodes constructed using platinum sponge.

The sensitivity of the electrochemical detector 100 which operates by an oxidation-reduction reaction, is dependent upon the surface area 126 available for reaction. For this purpose the active electrode 118 has been designed in the configuration of a flat disk to maximize the surface area 126 available. The size of the active electrode 118 is only limited by the size of the cavity 108. Other shapes for the active electrode 118 may also be used in the detector 100, such as square, rectangular and oval.

A contact lead 120 generally in the form of a strip is welded to the back of the active electrode 118. The contact lead 120 can be fabricated from materials such as platinum, palladium and gold. It has been found that the construction of the contact lead 120 in the form of a strip provides for increased support of the active electrode 118 when welded thereto. The active electrode 118 can be attached to any shape contact lead 120 which will conduct the current created from the oxidation-reduction reaction occurring on the surface area 126 of the active electrode 118, through the side wall of the housing 102 of the detector 100. In the preferred embodiment the contact lead 120 is constructed of a platinum strip as illustrated in FIG. 2.

The active electrode 118 as illustrated in FIG. 2 is adapted for measuring the concentration of a reducing agent such as hydrazine in a large volume of fluid such as in beaker samples or in the detection 100 of this invention. The use of a large disk for the active electrode 118 does not readily adapt itself for determining the presence of the reducing agent in small samples such as required when analyzing tissue samples of humans or animals. For this purpose, according to another embodiment of this invention, an active point electrode 132 as a probe is provided. The point electrode 132 is fabricated by first providing a conductive supporting wire 134 of a material inert to the reducing agent such as platinum, gold or palladium. The supporting wire 134 is coated at one end with the mixture of platinum sponge and platinum oxide. As it would be generally difficult to compress the platinum sponge and platinum oxide mixture around the supporting wire 134 to form a coating 136, a quantity of conductive resin as described above is mixed into the mixture to provide the structural integrity of the point electrode 132 during use. The conductive resin is included in the platinum sponge and platinum oxide mixture at all ratios of platinum sponge to platinum oxide in an amount up to about 20% by weight. The supporting wire 134 after being coated with the coating 136 which includes the conductive resin, is heated to an appropriate temperature to cure the resin to form a fully cured coating 136 which will maintain its structural integrity during use in the presence of the reducing agent such as hydrazine. The end of the supporting wire 134 having the coating 136 thereon is cut in a plane generally transverse to the axis of the supporting wire 134 to expose an annular end region 138 which becomes the active surface region of the point electrode 132. The annular end region 138 thus allows the point electrode 132 to be used as a probe for detecting the presence of a reducing agent in small samples at localized locations such as within tissue samples as previously noted.

The electrochemical detector as thus far described has been found suitable for measuring the concentration of strong reducing agents such as hydrazine that will reduce platinum oxide to platinum and compounds containing hydrazine such as acetylhydrazine, 1,1-dimethylhydrazine, methylhydrazine and sym-dimethylhydrazine. Additionally, it has been found that other reducing agents such as aminomorpholine, trimethylhydroquinone, cathechol and norepinephrine have been found detectable according to the electrode assembly and probe of this invention. Although only a limited number of reducing agents have been identified to be detected using the electrode assembly and method of the present invention, it should be clear to one skilled in the art that there are a large number of other strong reducing agents which will reduce platinum oxide to platinum and accordingly fall within the teachings of the present invention as being suitable for determining their concentration in a fluid sample according to this invention.

The operation of the electrochemical detector 100 according to this invention is based upon the principle of an oxidation-reduction reaction which generates a voltage proportional to the concentration of the reducing agent present which is reacting with the active electrode 118 within the detector. The electrode assembly 116 according to this invention has been found to be sensitive for the measurement of the concentration of the reducing agents generally in the one picogram range.

The operation of an electrochemical detector according to this invention is now described with reference to FIG. 4. The electrode assembly 116 including the counter-electrode 122 and active electrode 118 is placed within a cavity 108 of the housing 102. The counter-electrode 122 is placed adjacent to the outlet 114 and the active electrode 118 is placed adjacent to the inlet 112. The surface area 126 of the active electrode 118 is positioned to be generally parallel with the surface of the upper and lower halves 104, 106. The distance between the active electrode 118 and the counter-electrode 122 is generally in the range of approximately 2 mm to 10 mm depending on the size of the cavity 108. If the counter-electrode 122 and the active electrode 118 are positioned too close to each other, there is a danger of electrically shorting the counter-electrode with the active electrode thereby rendering the electrical chemical detector inoperative. As it is generally desired to construct the electrochemical detector 100 as small as possible, a suitable spacing for the active electrode 118 from the counter-electrode 122 has been found to be generally 2–5 mm.

A suitable electrolyte solution 140 containing the reducing agent such as hydrazine or its derivatives, is introduced as a sample fluid into the cavity 108 of the detector 100 through the inlet 112. The selection of a suitable electrolyte is known to those skilled in the art and includes solutions such as buffered water and tert-butylperchlorate. The electrolyte solution 140 containing the reducing agent is allowed to pass through the cavity 108 in a manner to pass over the surface area 126 of the active electrode 108 and then to contact the counter-electrode 122 before exiting from the detector 100 through the outlet 114. The electrolyte solution 140 is passed through the detector 100 at a generally uniform flow rate. As the electrolyte solution 140 passes over the surface 126 of the active electrode 118, the reducing agent present reacts with the platinum oxide on the surface area 126 to reduce the platinum oxide to platinum thereby creating an electrode potential which is proportional to the concentration of the reducing agent present within the electrolyte solution 140.

It is contemplated by way of explanation of the operation of the detector 100 for measuring the concentration of hydrazine that the reaction of hydrazine with the platinum oxide converts the hydrazine to ammonia and nitrogen. The active electrode 118 has been found to be useful for detecting the presence of the reducing agent present, such as hydrazine, over a long period of time indicating the non-consumable nature of the active electrode 118. It is contemplated that the reduced platinum oxide is subsequently oxidized spontaneously to the oxide by the reaction with oxygen within the electrolyte solution. The oxidation-reduction reaction occurring on the surface area 126 is thus enhanced by the use of platinum sponge over platinum oxide due to the increase in surface area. The increase surface area is thus seen to increase the sensitivity of the detector 100 as previously described. It is further contemplated that the counter-electrode 122 is generally not actively involved in the oxidation-reduction reaction and serves to pass the current generated between the counter-electrode and the active electrode 118 through the electrolyte solution 140. The contemplated explanation of the chemical reaction occurring within the detector 100 during operation is not intended to be a limitation on this invention as it is only given by way of suggested explanation of the oxidation-reduction reaction occurring within the detector 100.

The current flowing between the counter-electrode 122 and the active electrode 118 as a result of the oxidation-reduction reaction is amplified by the amplifier 128 (See FIG. 1) for amplification to a suitable level for accurately determining the concentration of the reducing agent within the electrolyte solution 140. Where the reducing agent is present in a sufficient quantity, the amplifier 128 may be eliminated and the current directly measured by a current or voltmeter for determining the concentration of the reducing agent within the electrolyte solution 140.

The detector 100 as described does not require the impressing of a current or other potential across the counter-electrode 122 and active electrode 118 for operation. In this manner, the detector 100 is suitable for use at multiple locations within the work environment as a self-contained detector. The detector 100 being compact and inexpensive to fabricate can be constructed in multiple units and positioned anywhere within the work environment, easily, and at relatively low cost. Where necessary, a central amplifier and control unit may be provided for monitoring the concentration of the reducing agents present within the air such as hydrazine at the locallized areas where there is provided a detector 100 according to this invention. The wires 124, 124' from the detector 100 may thus conveniently be connected to a centrallized control room.

The detector 100 has been described as including a housing 102 which includes the electrode assembly 116 having a counter-electrode 122 and active electrode 118 contained therein. As also described according to another embodiment of this invention as illustrated in FIG. 3, an active point electrode 134 may be used in place of the active electrode 118. The operation of the point electrode 134 is similar to that described with reference to the active electrode 118 within the detector 100. The point electrode 134 is positioned proximate to a counter-electrode 122 in a tissue sample which is of sufficient conductivity to provide the electrolyte solution to allow the current to flow between the counter-electrode 122 and active point electrode 132. The current generated by the electrode potential from the oxidation-reduction reaction occurring on the annular region 138 of the point electrode 134 is conducted to a suitable amplifier for measuring the concentration of the reducing agent present as thus described.

In accordance with this invention, a detector 100 was constructed to include a counter-electrode 122 and an active electrode 118. The counter-electrode 122 was constructed of a platinum wire about 0.127 in diameter and approximately 1 cm in length. The active electrode 118 was fabricated from a mixture of finely divided platinum sponge and platinum oxide in the ratio of about 7/1. The platinum sponge and platinum oxide were obtained from Alpha Metals, of New Jersey. Platinum oxide is available commercially in several isomers which vary in their molar water content. It has been found that an active electrode 118 fabricated from one isomer results in a more sensitive active electrode than an electrode fabricated from another isomer. In particular, an active electrode 118 fabricated from platinum oxide that had a noticeable brown color was more sensitive and preferred to an active electrode fabricated from platinum oxide having a noticeable black color. The selection of a particular platinum oxide isomer that gives maximum sensitivity can be easily achieved by fabricating sample active electrodes from different isomers and measuring their sensitivity with a known quantity of a reducing agent.

The above mixture was compressed in a die to produce an active electrode 118 of about 1 cm in diameter and about 0.2 mm in thickness. The active electrode 118 and counter-electrode 122 were spaced from each other approximately 2–5 mm within the housing 102 of the detector 100. A predetermined quantity (1 microgram sample per microliter electrolyte) of a reducing agent as listed in Table I was provided in a buffered water solution acting as an electrolyte and introduced as a 10 microliter sample into the detector 100. The results of the average of approximately 10 samples per reducing agent tested is disclosed in Table I. The electrode potential created during the oxidation-reduction reaction occurring on the surface of the active electrode 118 with the platinum oxide was measured and recorded by a strip recorder whose peak height is known to be proportional to the concentration of the reducing agent present within the sample. The results indicated in Table I, show that the electrode assembly 116 having an active electrode 118 and a counter-electrode 122 in accordance with this invention is suitable for measuring the concentration of hydrazine and its derivatives that are reducing agents as well as non-hydrazine reducing agents such as aminomorpholine, trimethylhydraquinone, cathechol and norepinephrine.

TABLE I

| Reducing Agent | Redox Potential (mV)* | Weight Response** | Relative Molar Response Relative to Hydrazine Hydrate |
|---|---|---|---|
| Hydrazine Hydrate | −201.5 | 8.0 | 1.0 |
| Acetylhydrazine | −77.8 | 0.9 | 0.1 |
| Methylhydrazine | — | 4.0 | 0.5 |
| 1,1-Dimethylhydrazine | 19.1 | 3.1 | 0.3 |
| sym-Dimethylhydrazine | 57.0 | 3.1 | 0.3 |
| Aminomorpholine | 103.3 | 1.0 | 0.1 |
| Trimethylhydroquinone | — | 0.9 | 0.05 |
| Catechol | — | 2.6 | 0.2 |
| Norepinephrine | — | 2.8 | 0.1 |

*Measured in pH 7.00 buffer with a redox pontial of 341.6 mV.
**Weight response equal to peak height/5 microliters per injection Accordingly, there has been described an electrochemical detector for determining the concentration of a reducing agent including hydrazine and hydrazine containing compounds contained within a sample fluid by an electrode potential created by an oxidation-reduction reaction occurring within the detector. The detector includes a housing having an inlet and outlet for passing the reducing agent therethrough. An active electrode is placed within the housing and is formed from a mixture of finely divided platinum sponge and platinum oxide in the weight ratio of from 1/1 to 20/1 and is further constructed to retain its structural integrity during use. A counter-electrode is located within the housing and is placed proximate to the active electrode. The electrodes are electrically connected to a device for measuring the electrode potential created by the oxidation-reduction reaction occurring within the detector to determine the concentration of the reducing agent within the sample fluid.

Further, according to this invention there is provided a method for determining the concentration of a reducing agent capable of reducing platinum oxide to platinum which includes fabricating an active electrode from a mixture of finely divided platinum sponge and platinum oxide constructed to retain its structural integrity during use. The active electrode is placed proximate to a counter-electrode, which electrodes are brought into contact with the reducing agent. The electrode potential created during the oxidation-reduction reaction occurring between the reducing agent and the electrodes is measured and the concentration of the reducing agent present is determined to be proportional to the electrode potential measured.

Although the invention herein has been described with reference to particular embodiments, it is to be understood that these embodiments are merely illustrative of the principles and application of this invention. Thus, it is to be understood that numerous modifications may be made in the illustrative embodiments and other arrangements may be devised without departing from the spirit and scope of this invention.

What is claimed is:

1. A method for determining the concentration of a reducing agent in a fluid, which is capable of reducing platinum oxide to platinum, comprising the steps of fabricating an active electrode from a mixture of platinum and platinum oxide constructed and arranged to retain its structural integrity during use, placing said active electrode proximate to a counter-electrode, bringing said electrodes in contact with said reducing agent in said fluid, and measuring the electrode potential created from an oxidation-reduction reaction occurring between said electrodes and said reducing agent.

2. The method as set forth in claim 1 further including placing said electrodes within a housing having an inlet and outlet and passing said fluid containing said reducing agent through said housing between said inlet and said outlet to contact said electrodes.

3. The method as set forth in claim 1 wherein said reducing agent is selected from the group consisting of hydrazine, acetylhydrazine, methylhydrazine, 1,1-dimethylhydrazine and symdimethylhydrazine.

4. The method as set forth in claim 1 wherein said reducing agent is selected from the group consisting of aminomorpholine, trimethylhydroquinone, catechol and norepinephrine.

5. The method as set forth in claim 1 further including the step of adding to said mixture of platinum and platinum oxide a sufficient quantity of an electrically conductive resin to maintain the structural integrity of said active electrode during use.

6. The method as set forth in claim 5 further including the step of fabricating said active electrode from said mixture of platinum, platinum oxide and electrically conductive resin by coating a portion of an electrically conductive support with said mixture and forming an annular region surrounding said conductive support at one end thereof.

7. A method for determining the concentration of a reducing agent in a fluid, which is capable of reducing platinum oxide to platinum, comprising the steps of fabricating an active electrode from a mixture of platinum sponge and platinum oxide in the weight ratio of from 1/1–20/1 and constructed and arranged to retain its structural integrity during use, placing said active electrode adjacent a counter-electrode, bringing said electrodes in contact with said reducing agent in said fluid, measuring the electrode potential created from an oxidation-reduction reaction occurring between said reducing agent and said electrodes to determine the concentration of said reducing agent in said fluid.

8. The method as set forth in claim 7 wherein said reducing agent is selected from the group consisting of hydrazine, acethylhydrazine, methylhydrazine, 1,1-dimethylhydrazine and sym-dimethylhydrazine.

* * * * *